United States Patent
Parthasaradhi et al.

(10) Patent No.: US 7,521,553 B2
(45) Date of Patent: Apr. 21, 2009

(54) CRYSTALLINE FORMS OF LAMOTRIGINE

(75) Inventors: Reddy Bandi Parthasaradhi, Andhrapradesh (IN); Reddy Kura Rathnakar, Andhrapradesh (IN); Reddy Rapolu Raji, Andhrapradesh (IN); Reddy Dasari Muralidhara, Andhrapradesh (IN); Reddy Kesireddy Subash Chander, Andhrapradesh (IN)

(73) Assignee: Hetero Drugs Limited, Hyderabad, Andhrapradesh (IN)

( * ) Notice: Subject to any disclaimer, the term of this patent is extended or adjusted under 35 U.S.C. 154(b) by 0 days.

(21) Appl. No.: 10/508,099

(22) PCT Filed: Mar. 17, 2003

(86) PCT No.: PCT/IN03/00057

§ 371 (c)(1),
(2), (4) Date: Sep. 15, 2004

(87) PCT Pub. No.: WO2004/083191

PCT Pub. Date: Sep. 30, 2004

(65) Prior Publication Data

US 2005/0119265 A1    Jun. 2, 2005

(51) Int. Cl.
  *C07D 253/075*   (2006.01)
  *A61K 31/53*   (2006.01)
(52) U.S. Cl. ........................ 544/182; 514/241
(58) Field of Classification Search ........... 544/182; 514/241, 24

See application file for complete search history.

(56) References Cited

U.S. PATENT DOCUMENTS 4,602,017 A   7/1986   Sawyer et al.
7,132,570 B2   11/2006   Neckebrock et al.

FOREIGN PATENT DOCUMENTS

WO   WO 02/068398   9/2002

OTHER PUBLICATIONS

H.G. Brittain, Polymorphism in pharmaceutical solids, Marcel Dekker Inc., New York (1999), pp. 1-2 and 195.

*Primary Examiner*—Deepak Rao
(74) *Attorney, Agent, or Firm*—Caesar, Rivise, Bernstein, Cohen & Pokotilow, Ltd.

(57) ABSTRACT

The present invention relates to novel crystalline forms of lamotrigine, to processes for their preparation and pharmaceutical compositions containing them.

9 Claims, 3 Drawing Sheets

CRYSTALLINE FORMS OF LAMOTRIGINE

This application is a 371 of PCT/IN03/00057 filed Mar. 17, 2003.

FIELD OF THE INVENTION

The present invention relates to novel crystalline forms of lamotrigine, to processes for their preparation and pharmaceutical compositions containing them.

BACKGROUND OF THE INVENTION

Lamotrigine of formula (1):

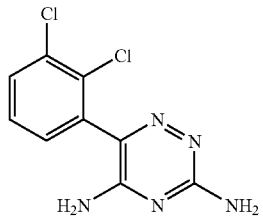

1 or 6-(2,3-Dichlorophenyl)-1,2,4-triazine-3,5-diamine is an anti-epileptic drug and its therapeutic uses are disclosed in U.S. Pat. No. 4,602,017.

Different synthetic methods of lamotrigine are described in WO 01/049669, U.S. Pat. No. 6,111,101, U.S. Pat. No. 6,333,198, U.S. Pat. No. 5,912,345, EP 800521, U.S. Pat. No. 4,602,017.

Various polymorphic forms are disclosed in WO 02/068398.

We have discovered three novel crystalline forms of lamotrigine. The novel forms have been found to be stable over the time and does not automatically convert into other crystalline forms of lamotrigine.

The novel forms of lamotrigine are, thus, suitable for pharmaceutical preparations.

Thus the object of the present invention is to provide stable novel crystalline forms of lamotrigine, to provide a processes for preparation of the novel crystalline forms and to provide a pharmaceutical compositions comprising these novel crystalline forms.

SUMMARY OF THE INVENTION

According to one aspect of the present invention, there is provided a novel crystalline Form I of lamotrigine characterized by an x-ray powder diffraction pattern having peaks expressed as 2θ at about 12.5, 13.9, 16.7, 18.0, 22.3, 23.6, 26.8, 27.9, 28.5, 28.9, 29.4, 31.7, 40.2, 42.3 degrees. FIG. 1 shows typical Form I x-ray powder diffraction pattern.

According to another aspect of the present invention, there is provided a novel crystalline Form II of lamotrigine characterized by an x-ray powder diffraction pattern having peaks expressed as 2θ at about 8.9, 11.2, 12.3, 13.2, 13.9, 17.0, 17.4, 18.0, 18.2, 18.7, 19.8, 21.4, 22.1, 22.7, 25.1, 25.4, 25.7, 26.4, 26.8, 27.1, 27.5, 28.3, 28.8, 29.2, 30.1, 30.9, 31.4, 32.9, 35.3, 35.7, 36.5 degrees. FIG. 2 shows typical Form II x-ray powder diffraction pattern.

According to another aspect of the present invention, there is provided a novel crystalline Form III of lamotrigine characterized by an x-ray powder diffraction pattern having peaks expressed as 2θ at about 9.9, 12.0, 13.3, 16.1, 17.0, 18.1, 18.7, 19.5, 24.4, 26.0, 26.3, 27.6, 28.1, 37.1 degrees. FIG. 3 shows typical Form III x-ray powder diffraction pattern.

According to another aspect of the present invention there is provided a process for preparation of Form I lamotrigine comprising the steps of:
a) dissolving lamotrigine in an ester;
b) maintaining at 15° C. to 30° C. for about 30 minutes to 2 hours;
c) filtering Form I lamotrigine.

The ester is selected from the group consisting of ethyl acetate, methyl acetate, ethyl formate, isopropyl acetate.

According to another aspect of the present invention there is provided a process for preparation of Form II lamotrigine comprising the steps of:
a) dissolving lamotrigine in dioxane;
b) maintaining at about 15° C. to about 30° C. for about 1 hour to 3 hours;
c) filtering Form II lamotrigine.

According to another aspect of the present invention there is provided a process for preparation of Form III lamotrigine comprising the steps of:
a) mixing lamotrigine, isopropyl acetate, chloroform and dimethyl formamide at about 60° C. to about 70° C.;
b) filtering the Form III lamotrigine at about 20° C. to about 30° C.

Lamotrigine prepared by any of the known methods can be used in the above processes. Lamotrigine solvate or hydrate may also be used in the above processes.

According to another aspect of the present invention there is provided a pharmaceutical composition comprising Form I or Form II or Form III lamotrigine.

x-Ray powder diffraction spectrum was measured on a Siemens diffractometer.

DETAILED DESCRIPTION OF THE INVENTION

Figure 1:
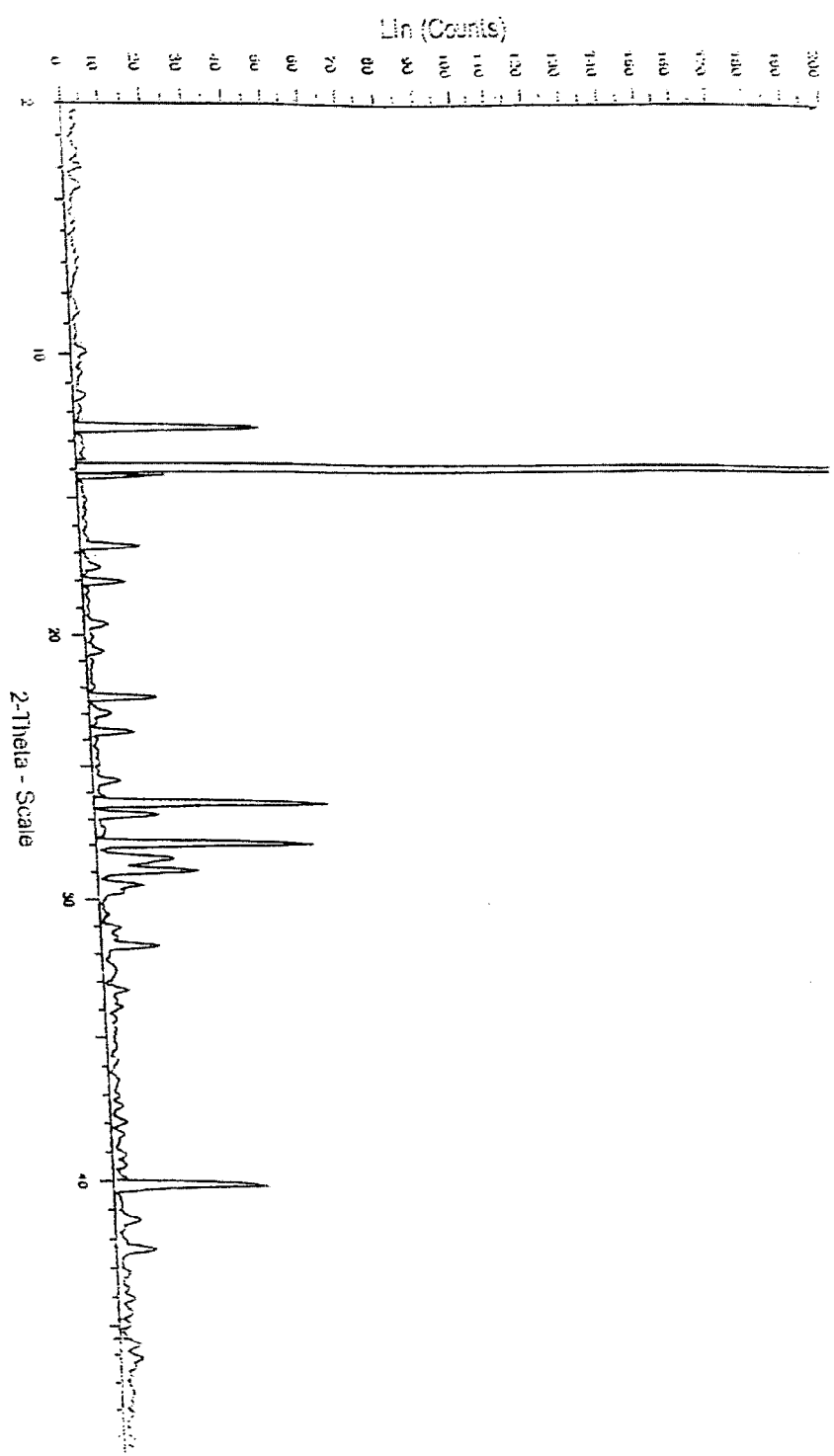
FIG. 1 is a x-ray powder diffraction pattern of Form I lamotrigine.

According to one aspect of the present invention, there is provided a novel crystalline Form I of lamotrigine characterized by an x-ray powder diffraction pattern having peaks expressed as 2θ at about 12.5, 13.9, 16.7, 18.0, 22.3, 23.6, 26.8, 27.9, 28.5, 28.9, 29.4, 31.7, 40.2, 42.3 degrees. FIG. 1 shows typical Form I x-ray powder diffraction pattern.

According to another aspect of the present invention, there is provided a process for preparation of Form I lamotrigine. Thus lamotrigine is dissolved in an ester. The ester is selected from the group consisting of ethyl acetate, methyl acetate, ethyl formate, isopropyl acetate. The Form I lamotrigine is maintained at about 15° C. to about 30° C., preferably at about 20° C. to about 25° C., for about 30 minutes to about 2 hours and filtered. Lamotrigine prepared by any of the known methods can be used in the process. Lamotrigine solvate or hydrate may also be used.

Figure 2:
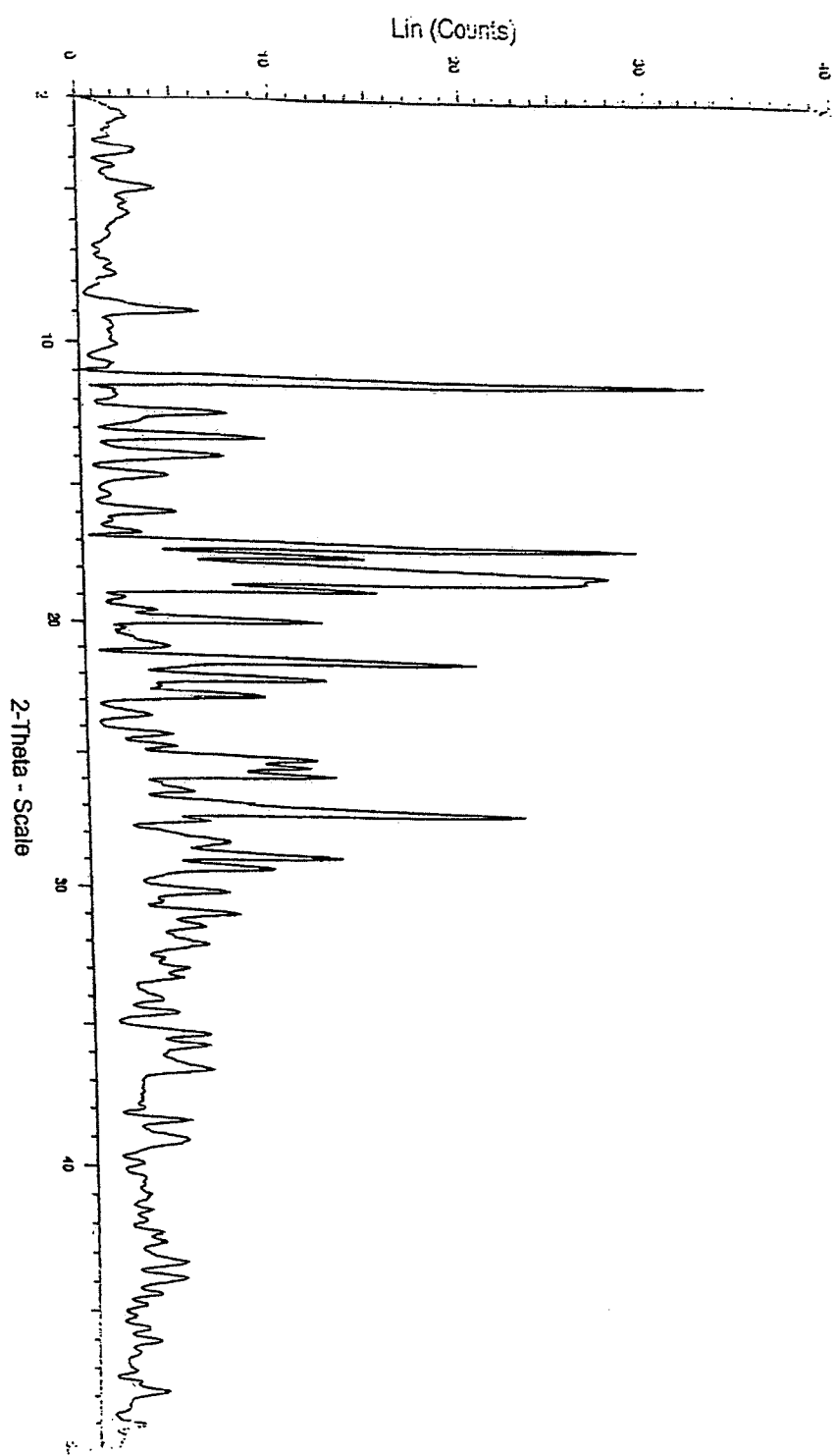
FIG. 2 is a x-ray powder diffraction pattern of Form II lamotrigine.

According to another aspect of the present invention, there is provided a novel crystalline Form II lamotrigine characterized by an x-ray powder diffraction pattern having peaks expressed as 2θ at about 8.9, 11.2, 12.3, 13.2, 13.9, 17.0, 17.4, 18.0, 18.2, 18.7, 19.8, 21.4, 22.1, 22.7, 25.1, 25.4, 25.7, 26.4, 26.8, 27.1, 27.5, 28.3, 28.8, 29.2, 30.1, 30.9, 31.4, 32.9, 35.3, 35.7, 36.5 degrees. FIG. 2 shows typical Form II x-ray powder diffraction pattern.

According to another aspect of the present invention there is provided a process for preparation of Form II lamotrigine. Thus lamotrigine is dissolved in dioxane and maintained at about 15° C. to about 30° C. for about 1 hour to 3 hours. The separated Form II lamotrigine is filtered. Lamotrigine prepared by any of the known methods can be used in the process. Lamotrigine solvate or hydrate may also be used.

Figure 3:
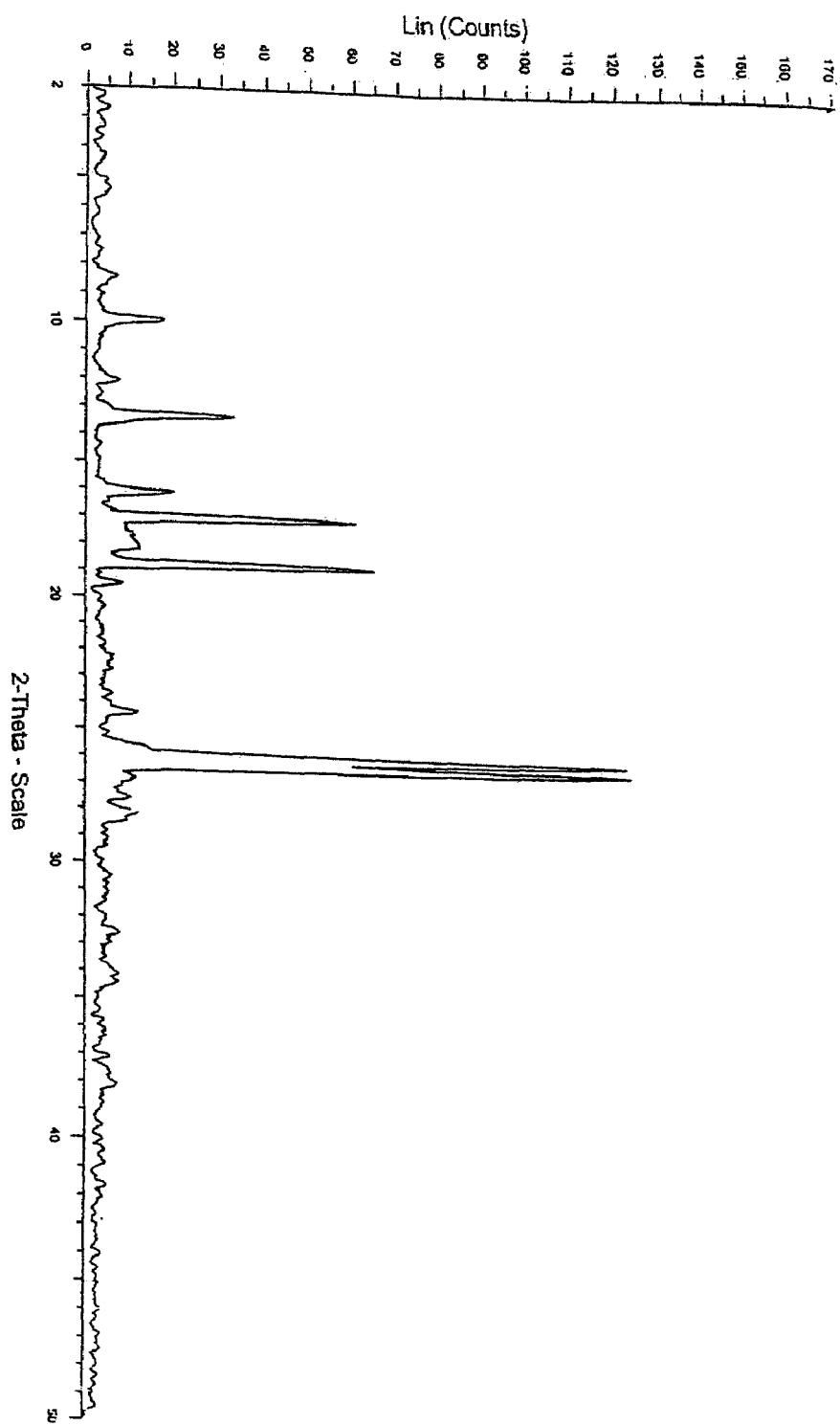
FIG. 3 is a x-ray powder diffraction pattern of Form III lamotrigine.

According to another aspect of the present invention, there is provided a novel crystalline Form III of lamotrigine characterized by an x-ray powder diffraction pattern having peaks expressed as 2θ at about 9.9, 12.0, 13.3, 16.1, 17.0, 18.1, 18.7, 19.5, 24.4, 26.0, 26.3, 27.6, 28.1, 37.1 degrees. FIG. 3 shows typical Form III x-ray powder diffraction pattern.

According to another aspect of the present invention there is provided a process for preparation of Form III lamotrigine. Thus lamotrigine isopropyl acetate, chloroform and dimethyl formamide are mixed and heated to about 60° C. to about 70° C. The contents are maintained for about 30 minutes and cooled to about 20° C. to about 30° C. The Form III lamotrigine is filtered. Lamotrigine prepared by any of the known methods can be used in the process. Lamotrigine solvate or hydrate may also be used.

According to another aspect of the present invention there is provided a pharmaceutical composition comprising Form I or Form II or Form III lamotrigine. The forms of lamotrigine may be formulated in a form suitable for oral administration or injection.

The following examples are given for the purpose of illustrating the present invention and should not be considered as limitations on the scope or spirit of the invention.

EXAMPLE 1

Lamotrigine (10 gm) (obtained by the process described in example 1 of U.S. Pat. No. 4,602,017) is mixed with ethyl acetate (100 ml) and maintained at about 70° C. for 30 minutes. Then the contents are cooled to about 20° C. The solid is separated by filtration to give 9.0 gm of Form I lamotrigine.

EXAMPLE 2

Lamotrigine (10 gm) (obtained by the process described in example 1 of U.S. Pat. No. 4,602,017) is added to dioxane (100 ml), maintained at 50° C. to 55° C. for 30 minutes, cooled to 25° C. and maintained at this temperature for 2 hours. The solid is separated by filtration to give 8.5 gm of Form II lamotrigine.

EXAMPLE 3

Lamotrigine (10 gm) (obtained by the process described in example 1 of U.S. Pat. No. 4,602,017) is added to isopropyl acetate (150 ml) and the contents are heated to about 65° C. Chloroform (50 ml) and dimethyl formamide (48 ml) are added at this temperature and stirred for 30 minutes. The contents are cooled to 25° C. and filtered to give 9.5 gm of Form III lamotrigine.

EXAMPLE 4

Example 1 is repeated using Form II lamotrigine instead of lamotrigine to give Form I lamotrigine.

EXAMPLE 5

Example 1 is repeated using Form III lamotrigine instead of lamotrigine to give Form I lamotrigine.

EXAMPLE 6

Example 2 is repeated using Form III lamotrigine instead of lamotrigine to give Form II lamotrigine.

EXAMPLE 7

Example 2 is repeated using Form I lamotrigine instead of lamotrigine to give Form II lamotrigine.

EXAMPLE 8

Example 3 is repeated using Form II lamotrigine instead of lamotrigine to give Form III lamotrigine.

EXAMPLE 9

Example 3 is repeated using Form I lamotrigine instead of lamotrigine to give Form III lamotrigine.

We claim:

1. A crystalline form of lamotrigine, characterized by an x-ray powder diffraction pattern having peaks expressed as 2θ at about 12.5, 13.9, 16.7, 18.0, 22.3, 23.6, 26.8, 27.9, 28.5, 28.9, 29.4, 31.7, 40.2, and 42.3 degrees.

2. A crystalline form of lamotrigine, characterized by an x-ray powder diffraction pattern as illustrated in FIG. 1.

3. A process for the preparation of Form I lamotrigine as defined in claim 1, comprising the steps of:
   a) dissolving lamotrigine in an ester;
   b) maintaining at 1° C. to 30° C. for about 30 minutes to 2 hours;
   c) filtering Form I lamotrigine;
   wherein the ester is selected from the group consisting of ethyl acetate, methyl acetate, ethyl formate, and isopropyl acetate.

4. A crystalline form of lamotrigine, characterized by an x-ray powder diffraction pattern having peaks expressed as 2θ at about 8.9, 11.2, 12.3, 13.2, 13.9, 17.0, 17.4, 18.0, 18.2, 18.7, 19.8, 21.4, 22.1, 22.7, 25.1, 25.4, 25.7, 26.4, 26.8, 27.1, 27.5, 28.3, 28.8, 29.2, 30.1, 30.9, 31.4, 32.9, 35.3, 35.7, and 36.5 degrees.

5. A crystalline form of lamotrigine, characterized by an x-ray powder diffraction pattern as illustrated in FIG. 2.

6. A process of preparing the Form II lamotrigine of claim 4, comprising the steps of:
   a) dissolving lamotrigine in dioxane;
   b) maintaining at about 15° C. to about 30° C. for about 1 hour to 3 hours; and
   c) filtering Form II lamotrigine.

7. A crystalline form of lamotrigine, characterized by an x-ray powder diffraction pattern having peaks expressed as 2θ at about 9.9, 12.0, 13.3, 16.1, 17.0, 18.1, 18.7, 19.5, 24.4, 26.0, 26.3, 27.6, 28.1, and 37.1 degrees.

8. A crystalline form of lamotrigine, characterized by an x-ray powder diffraction pattern as illustrated in FIG. 3.

9. A process for the preparation of Form III lamotrigine of claim 7, comprising the steps of:
   a) mixing lamotrigine, isopropyl acetate, chloroform and dimethyl formamide at about 60° C. to about 70° C.;
   b) filtering the Form III lamotrigine at about 20° C. to about 30° C.

\* \* \* \* \*